(12) United States Patent
Withagen et al.

(10) Patent No.: US 12,042,327 B2
(45) Date of Patent: Jul. 23, 2024

(54) STATIC GAIN CALIBRATION

(71) Applicant: KONINKLIJKE PHILIPS N.V., Eindhoven (NL)

(72) Inventors: Petrus Johannes Withagen, Halsteren (NL); Erik Hummel, Eindhoven (NL); Fred Simon Berend Van Nijnatten, Eindhoven (NL); Joost Adrianus Van Rooijen, Best (NL); Peter George Van De Haar, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 332 days.

(21) Appl. No.: 17/601,784

(22) PCT Filed: Apr. 10, 2020

(86) PCT No.: PCT/EP2020/060300
§ 371 (c)(1),
(2) Date: Oct. 6, 2021

(87) PCT Pub. No.: WO2020/208217
PCT Pub. Date: Oct. 15, 2020

(65) Prior Publication Data
US 2022/0192621 A1  Jun. 23, 2022

(30) Foreign Application Priority Data
Apr. 10, 2019 (EP) ..................... 19168386

(51) Int. Cl.
*A61B 6/58* (2024.01)
*A61B 6/00* (2024.01)
(Continued)

(52) U.S. Cl.
CPC .............. *A61B 6/585* (2013.01); *A61B 6/032* (2013.01); *A61B 6/4085* (2013.01); *A61B 6/4441* (2013.01)

(58) Field of Classification Search
CPC ....... A61B 6/585; A61B 6/4085; A61B 6/032; A61B 6/4441; A61B 6/5205;
(Continued)

(56) References Cited

U.S. PATENT DOCUMENTS

2007/0269001 A1* 11/2007 Maschke .............. A61B 6/4441
378/38
2012/0305791 A1* 12/2012 Watanabe ............... G01T 1/247
250/394
(Continued)

FOREIGN PATENT DOCUMENTS

DE       10228135 B3    1/2004
WO      2018085316 A1   5/2018

OTHER PUBLICATIONS

International Search Report and Written Opinion of PCT/EP2020/060300, dated Jun. 16, 2020.
(Continued)

*Primary Examiner* — Irakli Kiknadze

(57) ABSTRACT

An X-ray system comprises an assembly that is moveable to different scan coordinates to acquire X-ray projection images at the different scan coordinates in a dynamic mode while the assembly is moving. The assembly is also moveable to a predetermined reference coordinate to acquire an X-ray projection image at the predetermined reference coordinate in a static mode while the assembly is resting. The X-ray system also comprises a processor configured to obtain dynamic gain calibration parameters from the X-ray projection images acquired in the dynamic mode at one of the different scan coordinates; obtain a static gain calibration parameter from the X-ray projection image acquired in the
(Continued)

static mode at the predetermined reference coordinate; and determine adjusted dynamic gain calibration parameters.

20 Claims, 2 Drawing Sheets

(51) Int. Cl.
*A61B 6/03* (2006.01)
*A61B 6/40* (2024.01)

(58) Field of Classification Search
CPC ....... A61B 6/4417; A61B 6/582; A61B 6/037; A61B 6/4291; A61B 5/0035; A61B 6/06; A61B 6/4028; A61B 6/586; A61B 6/584; A61B 6/4464; A61B 6/12; A61B 6/547; A61B 6/03; A61B 34/20; A61B 6/4266; A61B 6/4405; A61B 2090/3764; A61B 6/035; A61B 6/4482; A61B 6/0442; A61B 6/5258; A61B 6/42; A61B 6/4035; A61B 6/544; A61B 6/545; A61B 6/4233; A61B 6/58; A61B 6/583; A61B 6/0487; G06T 11/005; G06T 11/006; F04C 2270/041; G01T 7/00; G01T 1/1648; G21K 1/043; G21K 1/025; G21K 1/04; G01N 23/083; G01N 23/046

USPC ........................................................ 378/207
See application file for complete search history.

(56) References Cited

U.S. PATENT DOCUMENTS

| 2014/0014828 | A1  | 1/2014 | Bredno |
| 2014/0044232 | A1* | 2/2014 | Liu .......................... H04N 5/32 |
| | | | 378/62 |
| 2014/0185781 | A1* | 7/2014 | Reitz ....................... G01T 1/247 |
| | | | 378/207 |
| 2015/0103972 | A1  | 4/2015 | Bredno |
| 2016/0015357 | A1  | 1/2016 | Rozas |
| 2017/0042498 | A1  | 2/2017 | Song |
| 2017/0238897 | A1  | 8/2017 | Siewerdsen |
| 2019/0269378 | A1* | 9/2019 | Lautenschlaeger .. G01N 23/046 |

OTHER PUBLICATIONS

Daly, M.J. et al "Geometric Calibration of a Mobile C-Arm for Intraoperative Cone-Beam CT", Medical Physics, vol. 35, No. 5, May 2008.

\* cited by examiner

STATIC GAIN CALIBRATION

CROSS-REFERENCE TO PRIOR APPLICATIONS

This application is the U.S. National Phase application under 35 U.S.C. § 371 of International Application No. PCT/EP2020/060300, filed on Apr. 10, 2020, which claims the benefit of European Patent Application No. 19168386.1, filed on Apr. 10, 2019. These applications are hereby incorporated by reference herein.

FIELD OF THE INVENTION

The present invention relates to X-ray systems, and to gain calibration methods for X-ray systems.

BACKGROUND OF THE INVENTION

To work accurately and reliably, sophisticated X-ray computed tomography (CT) or cone-beam computed tomography (CBCT) scanners require a full calibration carried out by field service engineers on a yearly basis. A heavily used CT or CBCT scanner demands an even more regular calibration, in which case an uncomplicated calibration procedure would provide the most cost-effective solution. Performing regular calibration scans is a time-consuming procedure during which the CT or CBCT scanner is unavailable for patient use and should thus be scheduled sufficiently in advance.

Gain calibration for image uniformity correction in flexible X-ray CT/CBCT systems has been described in document US 2015/0103972 A1 (BREDNO ET AL), Apr. 16, 2015 as a necessary consequence of the relative movements of system elements, amongst which source and detector. The relative movements of system elements are caused by the lacking structural rigidity in such flexible systems amplifying the effects of system wear, arm movement, etc. To achieve a gain calibration despite possible relative movements between system elements, a motion layer decomposition unit and method is disclosed, which decomposes acquired X-ray projection image data into indications of relative positions of the system elements at different gantry orientations. Sensor inputs may be contribute as further input data to the decomposition unit. A correction unit uses the so obtained indications of relative positions of the system elements at different gantry orientations to correct measured attenuation.

The proposed decomposition unit and method is deriving positional information for each system element, which makes gain calibration of typical multi-element X-ray systems more involved. Accurate gain calibration results are achieved for accurate measurements of the initial positions of the system elements only and additional sensor input to the decomposition unit may be needed to obtain satisfactory gain calibration. Moreover, the described method for gain calibration and uniformity correction acquires X-ray projection image data at each gantry position, which makes the calibration method a time-consuming one in flexible X-ray CT scanners for which a large variety of scan trajectories involving different arm movements exist and require each a dedicated calibration scan.

In view of the frequent and more widespread use of CT/CBCT scanners, faster and less demanding gain calibration methods are thus desirable.

SUMMARY OF THE INVENTION

There exists a trend towards a larger deployment of more flexible, open gantry X-ray imaging systems in image guided diagnostic and interventional procedures, e.g. in the medical fields of diagnosis and minimally invasive surgery relating to vascular, cardiovascular, non-vascular and neurological interventions or diagnosis. These more flexible, open X-ray systems for medical imaging offer better accessibility to and around the patient during interventional procedures and at the same time minimize unnecessary repositioning of the patient for the purpose of imaging. Together with fast acquisition protocols, this allows for time-saving procedures relying on image guidance, for instance in operating theatres an occupancy period of which is effectively reduced. A drawback of the more flexible, open X-ray systems is the reduced structural rigidity as compared to permanently installed CT scanners with closed gantries. This causes an increased sensitivity to mechanical vibrations, mechanical loads, dynamical forces during movements of the open gantry, etc., which all have a significant impact on the geometrical alignment of critical system components relative to each other, including components such as X-ray source, collimators and filters, X-ray detector, X-ray anti-scatter grid, and the like. For instance, the vibrations and bending forces which are respectively present in and exerted onto a flexible C-arm/C-arc during motion, rotation or acceleration, generally lead to a relative change in position between the X-ray tube in the source and the detector, which may have an anti-scatter grid attached to it. Even a small change in position between X-ray tube and detector causes noticeable changes in the white field exposure pattern detected by the detector. Shadows of the anti-scatter grid which are projected onto the detector may also shift significantly, depending on speed and acceleration of the C-arc. If not taking into account properly, e.g. by means of an adequate calibration method, these effects typically worsen the reconstructed image quality through the appearance of unwanted artifacts. This is first and foremost noticeable through a distorted detector gain during X-ray projection image acquisition, which gain dynamically deviates from the ideal gain recorded for an ideal, rigid system geometry for which the individual system components are not subject to a change in their respective positions.

It is therefore an objective of embodiments of the present invention to provide adequate gain calibration methods, and related X-ray imaging systems applying the same, for reducing and/or correcting the unwanted time-dependent gain variations in an easy-to-operate and more expedite manner.

The above objective is accomplished by a method and device according to the present invention.

In accordance with one aspect, an X-ray system for imaging comprises an assembly which includes a source and a detector. The detector is arranged distantly from the source to detect radiation emitted by the source after traversal of an imaging region. The assembly is moveable to different scan coordinates defined by at least one scan trajectory around the imaging region to acquire X-ray projection images at a plurality of said scan coordinates in a dynamic mode while the assembly is moving. The assembly is also moveable to a predetermined reference coordinate to acquire an X-ray projection image at said reference coordinate in a static mode while the assembly is resting. At least one processing unit is comprised by the X-ray system and is configured for receiving a plurality of dynamic gain calibration parameters as first inputs, for obtaining a static gain calibration parameter as a second input and for determining, based on at least the received first inputs and the obtained second input, a plurality of adjusted dynamic gain calibration parameters corresponding to each of the plurality of dynamic gain calibration parameters. Each dynamic gain calibration parameter is obtained from an X-ray projection image acquired in the dynamic mode at one of the scan coordinates of the at least one scan trajectory during a dynamic gain calibration period. The static gain calibration parameter is obtained from an X-ray projection image acquired in the static mode at the predetermined reference coordinate during a static gain calibration period, and a start time for the static gain calibration period occurs later than a start time for the dynamic gain calibration period such that the static gain calibration period and the dynamic gain calibration period are not overlapping in time.

According to particular embodiments, the at least one processing unit is also configured for obtaining a further static gain calibration parameter as a third input and for determining the plurality of adjusted dynamic gain calibration parameters based on the received first inputs, the obtained second input and the obtained third input. The further static gain calibration parameter is obtained from an X-ray projection image acquired in the static mode at the predetermined reference coordinate during an initial static gain calibration period immediately following the dynamic gain calibration period. A start time for the initial static gain calibration period precedes the start time for the static gain calibration period such that the initial static gain calibration period and the subsequent static gain calibration period are not overlapping in time.

According to particular embodiments, the at least one processing unit is further configured for determining the plurality of adjusted dynamic gain calibration parameters at the end of or subsequently to the static gain calibration period.

In accordance with another aspect, a method for calibrating gain parameters of an X-ray system for imaging, which comprises a source and a detector including a plurality of pixel elements, is disclosed. The source and the detector are jointly moveable to different scan coordinates defined by at least one scan trajectory around the imaging region to acquire X-ray projection images at a plurality of said scan coordinates in a dynamic mode while moving and are also jointly moveable to a predetermined reference coordinate to acquire an X-ray projection image at said reference coordinate in a static mode while resting. The method comprises obtaining a plurality of dynamic gain calibration parameters, obtaining a static gain calibration parameter, and determining, based on at least the obtained plurality of dynamic gain calibration parameters and the obtained static gain calibration parameter, a plurality of adjusted dynamic gain calibration parameters corresponding to each of the plurality of dynamic gain calibration parameters. Each dynamic gain calibration parameter is obtained from an X-ray projection image acquired in the dynamic mode at one of the scan coordinates of the at least one scan trajectory during a dynamic gain calibration period. The static gain calibration parameter is obtained from an X-ray projection image acquired in the static mode at the predetermined reference coordinate during a static gain calibration period, and a start time for the static gain calibration period occurs later than a start time for the dynamic gain calibration period such that the static gain calibration period and the dynamic gain calibration period are not overlapping in time.

X-ray systems for imaging for which the herein described gain calibration methods are particularly useful are the more flexible, open gantry X-ray imaging systems such as mobile and permanently installed C-arm X-ray imaging systems. However, the herein described gain calibration methods are also applicable to conventional computed tomography (CT) X-ray imaging systems with a closed gantry.

It is an advantage of embodiments of the invention that a regular static gain (re-) calibration of an X-ray CT or CBCT system performed by the user or an experienced field engineer at the premises where the system is installed is expedited. This gain calibration can be carried out in a less time-consuming manner because not every single trajectory available to the system operator requires a corresponding rotational scan, but only a limited number of much faster static scans. Therefore, quality assurance is guaranteed even for frequently used X-ray CT and CBCT systems in a cost- and time-effective manner.

It is an advantage of embodiments of the invention that the static gain calibration leads to a reduction of artifacts in the reconstructed image data and that absorption coefficients can be determined more accurately.

It is an advantage of embodiments of the invention that the static gain calibration can be used for non-uniformity correction of acquired X-ray projection data and/or for the correction of reconstructed image data.

It is an advantage of embodiments of the invention that the static gain calibration can be easily incorporated into existing X-ray systems and scanning procedures, protocols, and the like.

It is an advantage of embodiments of the invention that the static gain calibration can also be used with more flexible or open X-ray systems such as mobile or fixedly installed C-arm X-ray systems.

It is an advantage of embodiments of the invention that the static gain calibration can use air scans for the gain calibration parameter adjustment and thus does not rely on a phantom.

It is an advantage of some embodiments of the invention that resulting parameters of a previous gain calibration, which, for example, were obtained during an initial calibration scan during installation of the X-ray system or during one or more regular service intervals, can be stored in data records on a storage unit of the X-ray system or on a network drive for re-use during a subsequent static gain calibration.

Particular and preferred aspects of the invention are set out in the accompanying independent and dependent claims. Features from the dependent claims may be combined with features of the independent claims and with features of other dependent claims as appropriate and not merely as explicitly set out in the claims.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The above and other aspects of the invention will be apparent from and elucidated with reference to the embodiment(s) described hereinafter.

BRIEF DESCRIPTION OF THE DRAWINGS

The invention will now be described further, by way of example, with reference to the accompanying drawings, in which.

Figure 1:
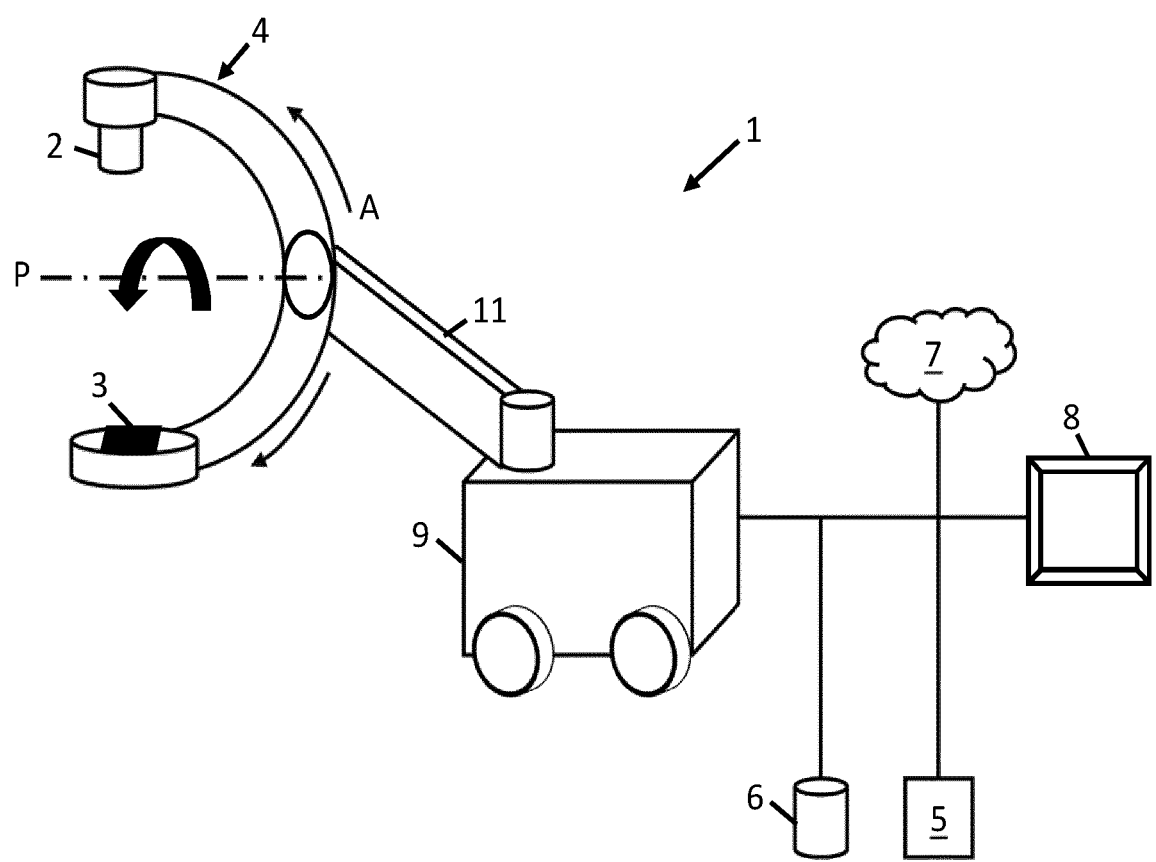
FIG. 1 shows a mobile C-arm X-ray imaging system in accordance with embodiments of the present invention.

The drawings are only schematic and are non-limiting. In the drawings, the size of some of the elements may be exaggerated and not drawn on scale for illustrative purposes. The dimensions and the relative dimensions do not necessarily correspond to actual reductions to practice of the invention.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

With reference to FIG. 1, an exemplary embodiment of a mobile C-arm X-ray imaging system 1 is shown. The mobile C-arm system 1 comprises an assembly 4, e.g. an arched mechanical support structure adopting a typical C-shape, which comprises a source 2 and a detector 3 provided at facing end portions thereof. X-ray radiation is generated and emitted by an X-ray source 2 and is traversing an imaging (volumetric) region of interest, in which X-ray radiation is scattered and/or absorbed, before it reaches a top surface of the detector 3 arranged distantly and opposite to the source 2. In subject or object scans, the emitted X-ray radiation is further scattered and/or absorbed by the subject (e.g. patient) or the object (e.g. phantom), in addition to the amount of scattering and absorption that occurs in air. The detector 3 converts the incident X-ray radiation signals into electrical signal suitable for image processing and reconstruction. The source to detector distance is typically such that an object to be scanned, e.g. a phantom, or a subject, e.g. a patient, fits in the air space in between, e.g. may range from 70 cm to 140 cm, e.g. about 100 cm. The source to detector distance may be fixed by design, neglecting the aforementioned positional variations that are small compared to the source to detector distance, or may be designed to be adjustable over a distance range. Although the source 2 is shown in a top position in FIG. 1, it is often preferable to operate the C-arm imaging system 1 in an under-couch configuration in which the source 2 is placed under a subject support (e.g. couch) for better radiation protection of the medical staff. The X-ray source 2 may comprise an X-ray generator block, e.g. DC converted block or high-frequency generator block, and an X-ray tube, e.g. fixed or rotating anode tube, to generate and emit X-rays. The emitted X-ray spectrum is typically polychromatic. Therefore, the C-arm imaging system 1 may further comprise one or more filter elements and/or beam shaping elements. A suitable X-ray detector 3 is preferably provided as a flat panel detector, meaning that X-ray imaging systems and calibration methods therefor are generally conceived for cone-beam CT. However, the calibration methods according to embodiments of the invention may also be applied to conventional fan beam CT scanners having a closed gantry, although the benefits for the latter may be less pronounced in view of their more rigid gantry structure. A pulsed source 2 is generally used if the detector 3 is provided as a flat panel detector. Flat panel detectors are of advantage in view of their lower height profile, which creates a large accessible space between the end portions of the C-arm assembly 4, their wider dynamic range, and also their distortion-free imaging quality. Alternatively, the detector 3 may comprise an image intensifier unit coupled to a camera unit.

The assembly 4 is mechanically connected, through an arm 11, to a mobile workstation 9. To collect X-ray projection image data at a plurality of scan coordinates, corresponding to different projection associated with different orientations and positions of the C-arm assembly 4 in space, the orientation of the C-arm assembly 4 in space can be controlled by a motion controller. For instance, the C-arm assembly 4 can be rotatable in a first direction A, e.g. by rotating it about a roll axis along the cranial/caudal angulation direction, and/or can be rotatable in a second direction P, e.g. by rotating it about a propeller axis along the right angular oblique/left angular oblique rotation direction. A movement about the propeller axis may be obtained by a revolution of the arm 11 itself or via a revolution of the C-arm assembly 4 in respect of the arm 11. At each of the different scan coordinates, the source 2 may be triggered to emit an X-ray pulse and the detector 3 to capture a corresponding X-ray projection image with an adequately set exposure time. Rotations about the propeller axis and/or the roll axis may be performed in steps to record a sequence of X-ray projection image data at various angulation and/or propeller angles for 2D or 3D image reconstruction of a volumetric imaging region of interest. To obtain the reconstructed image(s), available cone-beam CT image reconstruction algorithms known by the skilled artisan may be used such as the Feldkamp algorithm for cone-beam CT or variations thereof. A scan trajectory for a rotational scan may involve an angular scan range between 100 arc degrees and 360 arc degrees, e.g. between 100 arc degrees and 240 arc degrees. By example, the rotational scan is performed for angulation angles ranging between +90 arc degrees and −45 arc degrees and/or for propeller angles ranging from +135 arc degrees to −135 arc degrees.

A coordinate system for the C-arm may be defined with respect to the isocenter, e.g. x-axis in longitudinal or cranial/caudal direction, y-axis in transversal direction or left/right angular oblique (LAO/RAO) and z-axis in height direction or dorsal/ventral direction. The relative positions of the system components may then be indicated with respect to this coordinate system. Projection views for acquired X-ray projection images can be represented as oriented vectors or associated scan coordinates in such a coordinate system, as well as whole scan trajectories, which can be defined as a curve in the coordinate system. A scan trajectory's curve may be defined via a collection of connected scan trajectory points (e.g. scan coordinates) representing particular projection views along the curve. Interpolation techniques may be used to generate additional scan trajectory points to be placed in between the subsequent scan trajectory points in a collection of scan trajectory points (e.g. defined by an imaging protocol) and to be connected thereto if this improves the smoothness or path-specific aspects of the resulting curve, e.g. path-specific aspects relating to speed or acceleration of the open gantry, to allowable angulation and rotation ranges, image resolution, overall scan speed, and the like. For instance, it may be advantageous to provide options for both a fast scan trajectory with less X-ray image projections (e.g. views) being acquired, which reduces motion artifacts due to subject movements such as breathing, and a corresponding slow version of this scan trajectory for which more X-ray image projections (e.g. views) are acquired, which results in increased reconstructed image resolution.

The mobile work station 9 may comprise a display unit 8 providing a graphical user interface or, according to an alternative embodiment, may be connectable to a separate display unit providing a graphical user interface, e.g. a remote screen or an interactive touch screen. A display unit 8 with graphical user interface allows a customer-friendly interaction with the C-arm imaging system 1. Exemplary interactions may comprise the selection or definition of scan coordinates, scan trajectories, scan speeds, field of view, imaging protocols, acquisition modalities (e.g. source and detector settings), etc. Moreover, patient-specific details and reconstructed cone-beam CT images may be displayed by the display unit 8, including reconstructed images retrieved from memory or an image/patient database and reconstructed live images for use during image-guided diagnostics or interventional procedures. A medical practitioner may then select region of interests for carrying out an image analysis, contrast enhancements, size or length measurements, etc.

A storage unit 6 may be included in the mobile workstation 9. Alternatively, the storage unit 6 may be implemented as a separate, remote storage unit, e.g. as a centralized or distributed external storage unit, which can be part of a file hosting system, a server- or cloud-based storage service, etc. The storage unit 6 may store raw projection image data or data sets, e.g. a projection image data set comprising a sequence of X-ray projection images acquired for each of the scan coordinates of a scan trajectory. Additionally, the storage unit 6 may also store data records relating to the subject to be scanned, reconstructed images, data relating to the acquisition modalities, imaging system data provided by the manufacturer, calibration data, etc.

Furthermore, the mobile workstation 9 may also provide a wired or wireless network interface to be connectable to a network 7, e.g. a local area or wide area network such as a private secure network, a public network (e.g. the internet), a client-server communication network, etc. This brings about the benefits of a distributed application deployment, including, without being limited thereto, applications running as client-server applications, server- and cloud-based computing, remote (grid) computing, and the like. Besides, the access capability to a network may simultaneously the access to a remote storage unit/service. For example, the C-arm imaging system 1 including the workstation 9 may be adapted for sending acquired X-ray projection image data to a server for storage and/or for server-based image reconstruction. In return, the server may be configured for sending the reconstruction images back to the client workstation 9, e.g. for display or local archiving. One or more processing units 5 are comprised by the C-arm imaging system 1, e.g. may be comprised by the workstation 9 on the premises. Alternatively, some or all of the one or more processing units 5 may be at multiple locations, for instance, at different server locations in an imaging system 1 which relies on distributed processing. In such case, the one or more servers or remote computing devices represent the one or more processing units 5, which may be accessed by the workstation 9 via a network 7 or equivalent communication link. According to embodiments of the invention, the one or more processing units 5 are configured to perform steps of the gain calibration method, which steps are described in more detail further below. In addition thereto, the processing unit(s) 5 are generally configured to perform various image processing tasks, e.g. to perform uniformity correction or to perform the image reconstruction already mentioned before.

Figure 2:
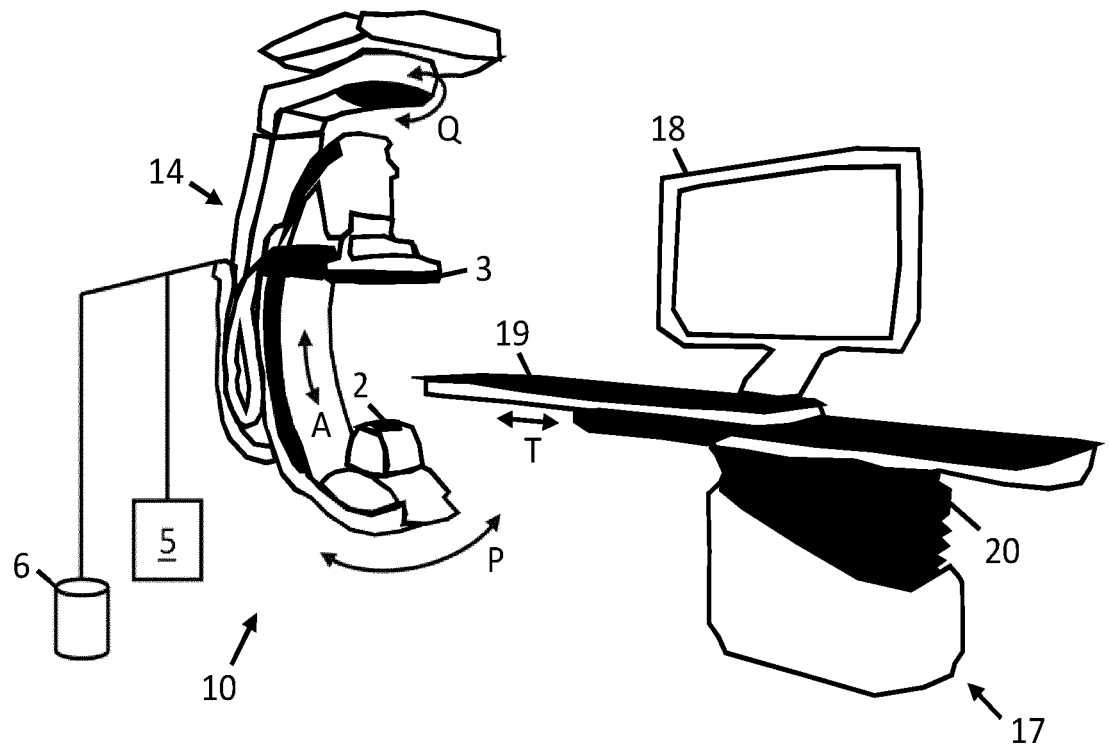
FIG. 2 shows a permanently installed C-arm X-ray imaging system in accordance with embodiments of the present invention.

With reference to FIG. 2, an exemplary embodiment of a permanently installed C-arm X-ray imaging system 10 is shown. Such a C-arm imaging system may be permanently installed through a ceiling mounting, which may include a ceiling-mounted rail system enabling transversal (lateral) and/or longitudinal displacements of the suspended C-arm/C-arc assembly 14, e.g. movement ranges in a transversal direction of up to two meters or more and movement ranges in a longitudinal direction of up to two meters or more (e.g. more than 4 m). Embodiments of the invention are not limited to ceiling-mounted open gantries; alternative embodiments may comprise floor-mounted C-arm assemblies, for example. The suspension mechanism for the C-arm assembly 14 may comprise a mechanical linkage with one or more joints. For instance, one or more revolute joints may enable a very flexible positioning of the suspended C-arm assembly 14 to gather X-ray projection images around a volumetric region of interest without compromising the accessibility to that region of interest, e.g. to a heart during positioning of a prosthetic valve. In FIG. 2, a revolute joint is illustrated, which enable a single axis rotation Q of the suspended C-arm assembly 14. Embodiments of the invention, however, are not limited to a single axis of rotation Q and the mechanical linkage for the C-arm assembly 14 may comprise other joints and links to provide further degrees of freedom, e.g. a rotatable L-arm for rotating the suspended C-arm assembly 14 around a turntable. The suspended C-arm assembly 14 itself typically allows for a two-axis rotation, providing two further degrees of freedom: a first rotational movement A in the cranial/caudal direction, also referred to as angulation about an roll-axis, and a second rotational movement P in the RAO/LAO direction, also referred to propeller rotation about a propeller axis. The two rotational movements A and P are enabling angular scans during which a plurality of X-ray projection images are gathered for the purpose of image reconstruction using computed tomography (CT), much like in a conventional closed gantry CT scanner, but providing more degrees of freedom and ensuring subject accessibility.

As an example, a C-arm imaging system 10 may comprise as many as eight degrees of freedom for positioning of the suspended C-arm assembly 14 and/or the collection of various X-ray projection views, e.g. along a scan trajectory. The various movements of the C-arm imaging system 10 are typically controlled by a motion controller or control system, e.g. a smart kinematic engine. The motion controller or control system may also store or receive as inputs standard predetermined or user-defined starting positions, e.g. the C-arm imaging system 10 can be provided with an accurate position memory recall functionality. Angular scan ranges along a scan trajectory may be given as 90 arc degrees for the first movement A in both the cranial and caudal direction and 120 arc degrees and 185 arc degrees for the second movement P in the LAO and ROA direction, respectively, if the C-arm assembly 14 is brought into a head position, or, if the C-arm assembly 14 is brought into a side position, given as 120 arc degrees and 185 arc degrees for the first movement A in the caudal and cranial direction, respectively 90 arc degrees for the second movement P in both the LAO and ROA direction.

The suspended C-arm assembly 14 also comprises an X-ray source 2 and an X-ray sensitive detector 3, which are arranged distantly from and are facing each other. In general, the X-ray source 2 and the detector 3 are firmly connected to or integrated into the respective end portion of the C-arm assembly 14. The source to detector distance may be adjustable and range between 80 cm and 130 cm. For air scans and subject scans the same as in the previous embodiment applies. Typical examples of X-ray sources 2 and detectors 3 are as previously described.

Next to the permanently installed C-arm imaging system 10, a turntable 17 is provided and cooperates with the C-arm imaging system 10. Especially the patient support 19 and the table pivoting unit 20 comprised by the turntable 17 are further complementing the degrees of freedom provided by the C-arm imaging system 10. By way of cooperation, the turntable 17 and the C-arm imaging system 10 may effectively form parts of an enlarged imaging system. For instance, a longitudinal translation T of the patient support may be used in combination with the various degrees of positioning of the C-arm imaging system 10. The translation T may be used for adjusting a longitudinal position of a subject or to extend the longitudinal scanning range of the C-arm imaging system 10, e.g. to obtain whole body coverage. It is also possible that the translation T allows for a shorter rail system installation in case of a suspended C-arc or avoids unnecessary movement thereof during a scan trajectory. Avoiding unnecessary movements can improve image quality, e.g. reduce reconstructed image artifacts, as a result of the smaller changes in relative positions of the imaging system components in the absence of motion or acceleration of the open gantry. In a similar manner, the table pivoting unit 20 may be controlled to incline the patient support 19 about a lateral and/or a longitudinal axis. This often allows for better subject accessibility during interventions or can be used as additional degrees of freedom when planning scan trajectories. For instance, the angulation range for the C-arm imaging system 10 may benefit from a larger scan range if the pivoting unit 20 is controlled to incline the patient support 19, e.g. about a longitudinal axis to extend the range of scannable RAO/LAO projection views, since a collision or restriction in movement between the turntable 17 and the source 2, for example, is thereby prevented. Eventually, the turntable 17 may be also height-adjustable.

According to some embodiments, one or more foot pedals, remote controls or voice command functionality may also be included in the C-arm imaging systems 1, 10 to provide (hand-free) user input to the imaging system. Such system input may encompass a starting command for executing a subject or air scan, to acquire a single X-raj projection image, to move the C-arm assembly 4, 14 to a default position (e.g. head position with zero default propeller and angulation rotation angles) or a start position for a scan trajectory.

Besides, the C-arm imaging system comprises one or more processing units 5 and may further comprise a display unit 18, a storage unit 6 and a network access interface (not shown). For these elements the same considerations as for the embodiment described in relation to FIG. 1 apply and are not repeated here.

As already mentioned, a large variety of scan trajectories is typically available for flexible C-arm imaging systems to cover the various imaging requirements and constraints that occur during image guided diagnostics or interventions. This implies that preferably every single scan trajectory available to the user or operator by virtue of such a flexible C-arm imaging system is individually calibrated in a calibration procedure. This is further supported by the fact that an upfront selection of scan trajectories is, in general, hard or impossible because the evolution of image guided diagnostics or interventions is often unpredictable, depending on many factors such as the available room in the operation room around the table, the number of intervening medical staff, the physiological characteristics of the patient, additional constraints on accessibility by equipment, tube and wires, etc. A fast rotational subject scan comprising a plurality of X-ray projection image acquisitions typically lasts for a few seconds, e.g. about four to five seconds, which is favorable for reducing motion artifacts. In contrast, a slower rotational subject scan or a scan relating to a more complex, optimized scan trajectory may last for several tens of seconds, e.g. up to 20 seconds or more. Therefore, a complete gain calibration procedure including all the available scan trajectories for the C-arm imaging system, in particular the slower ones, may last for several minutes, depending on the system, e.g. up to five minutes or more. A regular gain calibration for the plurality of X-ray projection images acquired at a corresponding plurality of scan coordinates along each scan trajectory is of uttermost importance for the quality assurance in clinical environments since irregularities in the gain directly translate into visible artifacts for the reconstructed images. This may lead to wrong medical findings and thus puts the patients at risk. Whereas a field engineer usually performs a full calibration (e.g. including a geometrical calibration in view of long-term drifts and system wear) of the X-ray imaging system on a yearly basis, more frequent service intervals are often recommendable for the dynamic (e.g. rotational) gain calibration. This may be accomplished on a weekly or daily basis in practice (e.g. at the start of every day), depending on the patient load/use of X-ray the imaging system and also on the required imaging quality. For procedures in the field of neurology, the required imaging quality is generally higher than for the imaging of the abdomen, for instance. Therefore, it is more cost-effective to provide a gain calibration method which can be easily carried out by the user at the premises, e.g. by the clinical staff. Here, dynamic or rotational gain calibration usually refers to the gain calibration along at least one, e.g. along each scan trajectory, of the X-ray imaging system, which involves the movement or acceleration of the gantry and hence is subject to bending or acceleration forces that lead to small but significant temporary changes in the relative positions of the various system components, such as source, detector and anti-scatter grid, that are involved in the projection image acquisition process. These momentary changes in the relative positions are dependent on the details of the selected scan trajectory, which makes the gain calibration dynamic and non-trivial. Especially for frequently used X-ray imaging systems, e.g. the mobile or flexible, permanently installed C-arm imaging systems, a faster dynamic gain calibration procedure, operated by the field engineer or the user, would allow for a higher daily patient load.

Embodiments of the invention provide such a faster dynamic gain calibration method, which will be described now with reference to the flowchart in FIG. 3. It is noted that the various method steps, as well as additional steps, are executable by the one or more processing units 5 of the X-ray imaging system (e.g. the C-arm imaging systems of the embodiments referred to in FIG. 1 and FIG. 2) in a technical implementation or can be performed in response to instructions of a software/computer program running on the one or more processing units 5.

Figure 3:
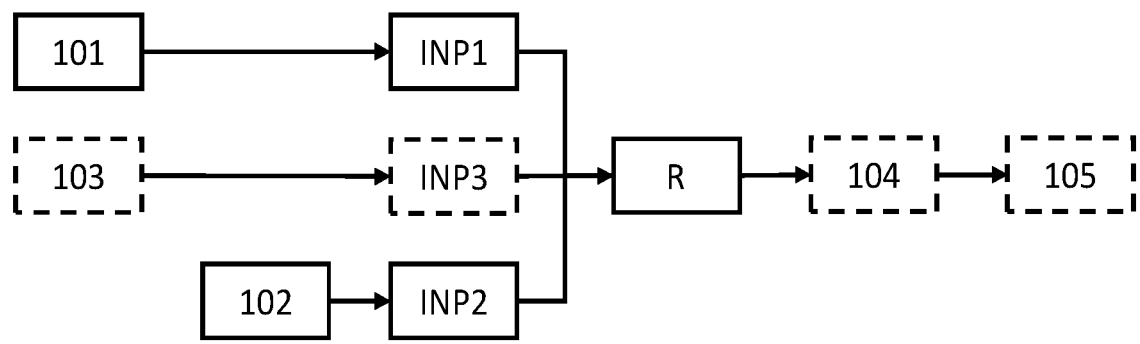
FIG. 3 is a flowchart of a method for calibrating gain parameters in an X-ray imaging system in accordance with embodiments of the present invention.

In FIG. 3, a plurality of dynamic gain calibration parameters are obtained, e.g. received as first inputs INP1 by the one or more processing units 5, and a static gain calibration parameter is also obtained, e.g. received or determined as a second input INP2 by the at least one processing unit 5. Next, a plurality of adjusted dynamic gain calibration parameters R is determined, wherein each of the plurality of adjusted dynamic gain calibration parameters R is a corresponding recalibrated value for one of the plurality of provided dynamic gain calibration parameters (e.g. first inputs INP1). Here, a single (adjusted) dynamic gain calibration parameter may be associated with a single pixel element of the detector of the X-ray imaging system for a given scan coordinate, e.g. may be the measured or extracted nominal gain for that pixel and for that given scan coordinate after offset correction. Alternatively, a single (adjusted) dynamic gain calibration parameter may be associated with a group of pixel elements of the detector of the X-ray imaging system for a given scan coordinate, e.g. may be the measured or extracted average nominal gain for that group of pixels and for that given scan coordinate after offset correction, i.e. the spatially averaged gain for a block of pixels for that given scan coordinate. It is noted that this naturally leads to a sequence or series of (adjusted) dynamic gain calibration parameters, wherein each (adjusted) dynamic gain calibration parameter within the sequence is linked to a given scan coordinate within a corresponding sequence of scan coordinates of a scan trajectory selected for dynamic gain calibration. For each scan coordinate along a scan trajectory, for example, a corresponding gain pixel map may be obtained, e.g. received as first inputs INP1 by the at least one processing unit 5. The plurality of dynamic gain calibration parameters may be retrieved from a database or data record in a data store, e.g. retrieved from a local or remote storage unit 6 of the C-arm imaging systems 1, 10. According to the gain calibration method, each dynamic gain calibration parameter is obtained from an X-ray projection image acquired in a dynamic mode at one of the scan coordinates of at least one scan trajectory during a dynamic gain calibration period 101. Dynamic mode, in the context of the present invention, refers to a moving or accelerated assembly, e.g. open gantry, constituting a continuous motion (e.g. propeller or angulation rotations) between scan coordinates for which a corresponding projection view is recorded, e.g. by triggering the acquisition of an X-ray projection image upon reaching each scan coordinate. The dynamic gain calibration period refers to a time period during which the at least one scan trajectory has been scanned and the scan has been accomplished, e.g. the time span bridging the start time end the end time for the at least one scan trajectory.

Likewise, a single static gain calibration parameter may be associated with a single pixel element of the detector of the X-ray imaging system for a predetermined reference coordinate, e.g. may be the measured or extracted nominal gain for that pixel and for the reference coordinate after offset correction. Alternatively, a single static gain calibration parameter may be associated with a group of pixel elements of the detector of the X-ray imaging system for a predetermined reference coordinate, e.g. may be the measured or extracted average nominal gain for that group of pixels and for the predetermined reference coordinate after offset correction, i.e. the spatially averaged gain for a block of pixels for the predetermined reference coordinate. According to the gain calibration method, at least one static gain calibration parameter is obtained from an X-ray projection image acquired in a static mode at the predetermined reference coordinate during a static gain calibration period 102. Static mode, in the context of the present invention, refers to a resting, non-accelerated assembly, e.g. open gantry, for which a corresponding projection view is recorded, e.g. by triggering the acquisition of an X-ray projection image (or several X-ray projection images for the purpose of averaging and noise reduction) at the predetermined reference coordinate. The reference coordinate may be a default position of the X-ray imaging system specified by the manufacturer or may be a user-defined position of the X-ray imaging system, e.g. a commonly used starting position in procedures such as, for example, a head position at zero angles for the rotation directions A and P and the source 2 and the detector 3 being in a lower position and upper position, respectively. The static gain calibration period refers to a time period during which the one or more static scan acquisitions have been accomplished, e.g. the time span bridging the start time end the end time for a single static acquisition at the reference coordinate. If the one or more static scan acquisitions at the reference coordinate are made immediately after accomplishing a scan trajectory selected for gain calibration, the static gain calibration period may also include the time interval that is necessary to bring back the assembly to the reference coordinate.

In a minimal embodiment the X-ray projection data acquired for a single pixel element or a single average of pixel elements at the reference coordinate is the basis for determining a single static gain calibration parameter as second input INP2, whereas the sequence of X-ray projection data acquired for this single pixel element or this single average of pixel elements at each scan coordinate of the scan trajectory undergoing gain calibration is the basis for determining a plurality of dynamic gain calibration parameters as first inputs INP1. In particular embodiments, however, multiple X-ray projection data acquired for multiple pixel elements of the detector at the reference coordinate, e.g. each pixel element of the detector, is the basis for determining multiple static gain calibration parameters as second inputs INP2, e.g. in the form of a static gain pixel map. Accordingly, the plurality of dynamic gain calibration parameters may be provided as first inputs INP1 in the form of a time-ordered series of dynamic gain pixel maps.

In accordance with the gain calibration method, the static gain calibration period occurs at a later moment in time than the dynamic gain calibration period, i.e. the static gain calibration period starts at a start time which is later than a start time for the dynamic gain calibration period and the static gain calibration period and dynamic gain calibration period do not overlap in time. According to particular embodiments of the invention, a static mode acquisition at the reference coordinate may occur during an earlier, initial static gain calibration period to provide further input(s) INP3 or may occur during a later static gain calibration period to provide second input(s) INP2, wherein earlier and later are assessed relative to the end time of the dynamic gain calibration period. Thus, if the static gain calibration period occurs at a later time than the dynamic gain calibration period in accordance with the gain calibration method, this may comprise cases for which each available scan trajectory is first scanned in the dynamic mode for providing the plurality of dynamical gain calibration parameters for each scan trajectory, and only at a later moment in time, the earlier, initial static gain period or the later static gain period starts with the first static acquisition at the reference coordinate. If more than one scan trajectory is available, other cases exist—for instance the case for which, after each individually accomplished scan trajectory, one or more static acquisitions are performed at the reference coordinate during an initial static gain calibration period before moving on to the next scan trajectory. At a later moment in time, after having cycled through all the available scan trajectories, the later static gain calibration period starts. Typically, an initial static gain calibration period, if provided so as to obtain further input(s) INP3, is scheduled closer in time to an end time of the dynamic gain calibration period than the (later) static gain calibration period which is always provided so as to obtain second input(s) INP2. In this respect, closer in time generally means within a few minutes or less (e.g. within five minutes or less, e.g. within one minute or less) such that an initial static gain calibration period, if provided, is directly following the dynamic gain calibration period, whereas the (later) static gain calibration period is not directly following it, but occurs at more distant moment in time, e.g. within a few days, a few weeks or even a few months from an end time of the dynamic gain calibration period, depending on the patient load and the required imaging quality, which determine the time interval before the dynamic gain is recalibrated through the provision of the adjusted dynamic gain calibration parameters.

In one particular embodiment, for example, all the available scan trajectories are scanned during the dynamic gain calibration period 101. The sequence of X-ray projection images associated with each individual scan trajectory is used to extract (after offset compensation) the plurality of dynamic gain calibration parameters, e.g. dynamic gain calibration pixel maps for each scan trajectory. This dynamic gain calibration period may occur at the time the X-ray imaging system has been manufactured, installed for the first time at the premises, or at scheduled moments of regular service intervals. The plurality of dynamic gain calibration parameters may then be stored in a database or as data records on a suitable data store for later use as first inputs INP1, e.g. on the storage unit 6 for the C-arm imaging systems 1, 10. It is possible to override or update initially recorded dynamic gain calibration parameters, e.g. as the result of a scheduled maintenance routine by a service engineer, and to later use the overwritten or updated dynamic gain calibration parameters as first inputs INP1 instead. Then, assuming a weekly quality assurance interval for the C-arm imaging systems 1, 10, the clinical staff is instructed to recalibrate the dynamic gain calibration parameters. In this particular embodiment, the clinical staff thus executes, each week, one or more static gain acquisitions in the static mode at the reference coordinate during the static gain calibration period 102, e.g. by triggering the one or more static gain acquisitions through a graphical user interface or by programming the C-arm imaging systems 1, 10 to schedule and perform (after confirmation for X-ray protection) the one or more static gain acquisitions automatically. From the offset-corrected static mode acquisition(s), at least one static gain calibration parameter is extracted and directly used as second input INP2 or stored for later use as second input INP2 upon query. Next, a plurality of adjusted dynamic gain calibration parameters R is determined as the recalibrated set of dynamic gain calibration parameters. This may be achieved by the one or more processing units 5 of the C-arm imaging systems 1, 10, for instance, by first receiving the stored dynamic gain calibration parameters, through a data request to the storage unit 6, as first inputs INP1 and by directly using or also receiving from the storage unit 6, the least one static gain calibration parameter as second input(s) INP2. A plurality of adjusted dynamic gain calibration parameters R may then be determined by the at least one processing unit 5 as $R(m,n)[i]=INP1(m,n)[i]*INP2(m,n)/D(m,n)$, for example. Here the index tuple (m,n) designate the adjusted dynamic/dynamic/static gain calibration parameter associated with the pixel element in the m-th row and the n-th column of the detector 3, and the single index [i] represents an index to the set of available scan trajectories. It is noted that the at least one static gain calibration parameter (e.g. INP2) is not dependent on a particular scan trajectory as it results from static mode acquisition(s) at the reference coordinate. The coefficients $D(m,n)$ in the denominator are acting as normalization constants. The coefficients $D(m,n)$ may or may not depend on the selected scan trajectory. They may be provided by the manufacturer as heuristically determined constants or single constant, or may be derived from the stored or extracted dynamic gain calibration parameters. For instance, the $D(m,n)$ may correspond to the dynamical gain calibration parameter pixel map that has been extracted from the last acquired dynamic mode X-ray projection image at the end of the dynamic gain calibration period. Alternatively, the $D(m,n)$ may correspond to an average of dynamical gain calibration parameter pixel maps that have been extracted from the multiple acquired dynamic mode X-ray projection images during the dynamic gain calibration period, e.g. the average over acquired dynamic mode X-ray projection images belonging to a single scan trajectory or over the acquired dynamic mode X-ray projection images of all available scan trajectories. In yet an alternative way, the $D(m,n)$ may be obtained by extrapolating a set of dynamical gain calibration parameter pixel maps associated with different scan speeds, e.g. by extrapolation to zero scan speed. Or, in still another way, the D(m,n) may correspond to a static gain calibration parameter pixel map that has been extracted from an acquired static mode X-ray projection image at a scan coordinate different from the reference coordinate, immediately after the end of the dynamic gain calibration period. Many other possibilities of providing adequate coefficients D(m,n) exist. As a result, the plurality of adjusted dynamic gain calibration parameters, R, are obtained for the recalibrated dynamic gain without having to carry out, again, the more time-consuming calibration scans for each scan trajectory. As already mentioned, the adjustments for the dynamic gain calibration parameters, resulting in the adjusted dynamic gain calibration parameters R, may be repeated many times, e.g. on a daily or weekly basis.

In another embodiment, all the available scan trajectories are scanned during the dynamic gain calibration period 101. The sequence of X-ray projection images associated with each individual scan trajectory is used to extract (after offset compensation) the plurality of dynamic gain calibration parameters, e.g. dynamic gain calibration pixel maps for each scan trajectory. This dynamic gain calibration period may occur at the time the X-ray imaging system has been manufactured, installed for the first time at the premises, or at scheduled moments of regular service intervals. The plurality of dynamic gain calibration parameters may then be stored in a database or as data records on a suitable data store for later use as first inputs INP1, e.g. on the storage unit 6 for the C-arm imaging systems 1, 10. It is possible to override or update initially recorded dynamic gain calibration parameters, e.g. as the result of a scheduled maintenance routine by a service engineer, and later use the overwritten or updated dynamic gain calibration parameters as first inputs INP1 instead. Immediately following the dynamic gain calibration period 101 (e.g. within a few minutes time, e.g. within less than one minute up to five minutes), one or more initial static acquisitions are performed at the reference coordinate in the static mode during an initial static gain calibration period 103 (e.g. t_start[103] >t_end [101]). From the initial static mode acquisition(s), at least one further static gain calibration parameter is extracted and stored for later use as third inputs INP3, e.g. stored together with the dynamic gain calibration parameters. At a later moment in time, e.g. later than the end of the initial static gain calibration period 103 at manufacture, first time installation or regular service moment, respectively, again one or more static acquisitions are performed at the reference coordinate in the static mode during an the static gain calibration period 102 (e.g. t_start[102]>t_end [103]). As for the previous example, the later moment in time may refer to the next day, week or month, depending on the patient load and the required imaging quality. From the later offset-corrected static mode acquisition(s), at least one static gain calibration parameter is extracted and directly used as second input INP2 or stored for later use as second input INP2 upon query. Next, a plurality of adjusted dynamic gain calibration parameters R is determined as the recalibrated set of dynamic gain calibration parameters. This may be achieved by the one or more processing units 5 of the C-arm imaging systems 1, 10, for instance, by first receiving the stored dynamic gain calibration parameters and the at least one further static gain calibration parameter, through a data request to the storage unit 6, as first inputs INP1 and third input(s) INP3, respectively, and by directly using or also receiving from the storage unit 6, the least one static gain calibration parameter as second input(s) INP2. A plurality of adjusted dynamic gain calibration parameters R may then be determined by the at least one processing unit 5 as R(m,n)[i]=INP1(m,n)[i]*INP2(m,n)/INP3(m,n), for example. Alternatively, for small time-dependent changes in the static gain calibration parameters, on may determine the adjusted dynamic gain calibration parameters R as R(m,n)[i]=INP1(m,n)[i]*(INP2(m,n)−INP3(m,n)). In yet an alternative way, the following functional expression may be used for cases for which a plurality of further static gain calibration parameters have been respectively obtained at the end of each scan trajectory selected for dynamic gain calibration: R(m,n)[i]= INP1(m,n)[i]*INP2(m,n)/INP3(m,n)[i]. As a result, the plurality of adjusted dynamic gain calibration parameters, R, are obtained for the recalibrated dynamic gain without having to carry out, again, the more time-consuming calibration scans for each scan trajectory. Also here, the adjustments for the dynamic gain calibration parameters, resulting in the adjusted dynamic gain calibration parameters R, may be repeated many times, e.g. on regular or irregular time intervals, e.g. on a daily or weekly basis.

In particular embodiments of the invention, the static acquisitions in the static mode and the dynamic acquisitions in the dynamic mode are performed in the absence of any object in the X-ray propagation region between the source 2 and the detector 3, e.g. are performed as static air acquisitions and dynamic air scans, respectively.

Determining static or dynamic gain calibration parameters by extraction from the acquired X-ray projection images may be performed by the same or a different processing unit compared to the processing unit used for determining the adjusted dynamic gain calibration parameters. The extraction of gain parameters from X-ray projection images typically involves the step of offset correction. Detector offset, however, is not affected, or at least not as significantly affected by the movements of the gantry/assembly 4, 14 of the X-ray imaging systems 1, 10 as the detector gain. In consequence, offset recalibration may be carried out by the field service engineer on a regular basis, e.g. each time the dynamic gain calibration parameters are overwritten or updated during regular maintenance.

The adjusted dynamic gain parameters R may be used to correct the non-uniformity of the detector 3 in an optional, subsequent non-uniformity correction step 104. Non-uniformity of the detector 3 is generally caused by any factors such as non-uniformity of the source 2, the presence of beam filtering elements, the shadows of the anti-scatter grid, etc. Changes in the uniformity of the detector 3 are also expected due to the temporary changes in the relative positions of the components of the X-ray imaging system. Non-uniformity of the detector 3, if not taken care of, causes severe artifacts in the reconstructed images. In a further optional step, the image reconstruction step 105, the acquired and uniformity corrected X-ray projection images for a subject scan trajectory or reconstructed to display a 2D or 3D view of the volumetric region of interest, e.g. displayed to a medical expert on the display unit 8 during an image-guided diagnostic or interventional procedure.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. Any reference signs in the claims should not be construed as limiting the scope.

The invention claimed is:

1. An X-ray system for imaging, comprising:
an assembly comprising a source and a detector, the detector arranged distantly from the source to detect radiation emitted by the source after traversal of an imaging region, wherein the assembly is moveable to different scan coordinates defined by at least one scan trajectory around the imaging region to acquire X-ray projection images at a plurality of the different scan coordinates in a dynamic mode while the assembly is moving and the assembly is moveable to a predetermined reference coordinate to acquire an X-ray projection image at the predetermined reference coordinate in a static mode while the assembly is resting;
at least one processor configured to:
receive a plurality of dynamic gain calibration parameters as first inputs, obtain a static gain calibration parameter as a second input, and
determine a plurality of adjusted dynamic gain calibration parameters corresponding to each of the plurality of dynamic gain calibration parameters based on at least the received first inputs and the obtained second input,
wherein:
each dynamic gain calibration parameter is obtained from an X-ray projection image acquired in the dynamic mode at one of the different scan coordinates of the at least one scan trajectory during a dynamic gain calibration period,
the static gain calibration parameter is obtained from the X-ray projection image acquired in the static mode at the predetermined reference coordinate during a static gain calibration period, and
a start time for the static gain calibration period occurs later than a start time for the dynamic gain calibration period such that the static gain calibration period and the dynamic gain calibration period are not overlapping in time.

2. The system according to claim 1, wherein the at least one processor is further configured to:
obtain a further static gain calibration parameter as a third input, and
determine the plurality of adjusted dynamic gain calibration parameters based on the received first inputs, the obtained second input and the obtained third input, the further static gain calibration parameter obtained from an X-ray projection image acquired in the static mode at the predetermined reference coordinate during an initial static gain calibration period immediately following the dynamic gain calibration period,
wherein a start time for the initial static gain calibration period precedes the start time for the static gain calibration period such that the initial static gain calibration period and the subsequent static gain calibration period are not overlapping in time.

3. The system according to claim 2, wherein the at least one processor is further configured to determine the plurality of adjusted dynamic gain calibration parameters at an end of the static gain calibration period or subsequently to the static gain calibration period.

4. The system according to claim 3, wherein each of the plurality of adjusted dynamic gain calibration parameters and the corresponding received dynamic gain calibration parameters is associated with a pixel element of the detector at one of the different scan coordinates and is determined according to a functional relationship: R=the first inputs * the second inputs/the third inputs, with the second input and the third input being associated with the pixel element of the detector at the predetermined reference coordinate.

5. The system according to claim 1, wherein the at least one processor is further configured to:
repeatedly obtain as the second input, at each of a plurality of time steps, the static gain calibration parameter obtained from the X-ray projection image acquired in the static mode at the predetermined reference coordinate during the static gain calibration period including a time step of the plurality of time steps, and
repeatedly determine, at each of the plurality of time steps, the plurality of adjusted dynamic gain parameters.

6. The system according to claim 1, wherein the at least one processor is further configured to at least one of: (i) receive X-ray projection images and extracting therefrom static and dynamic gain calibration parameters or (ii) perform an image uniformity correction on acquired X-ray projection image data, using the plurality of adjusted dynamic gain parameters.

7. The system according to claim 1, wherein the at least one processor is further configured to obtain an input by accessing a data record.

8. The system according to claim 1, wherein the at least one processor is further configured to determine a rotational gain parameter obtained at a first moment in time based on image projection data collected in a rotating mode.

9. The system according to claim 1, wherein the assembly further comprises a rotatable C-arm with two opposite end portions facing each other, the source and the detector being respectively coupled to one of the end portions.

10. The system according to claim 1, wherein the source is configured to emit radiation as a cone-beam.

11. A method for calibrating gain parameters of an X-ray system for imaging, the method comprising:
obtaining a plurality of dynamic gain calibration parameters,
obtaining a static gain calibration parameter, and
determining a plurality of adjusted dynamic gain calibration parameters corresponding to each of the plurality of dynamic gain calibration parameters based on at least the obtained plurality of dynamic gain calibration parameters and the obtained static gain calibration parameter,
wherein the X-ray system comprises a source and a detector including a plurality of pixel elements, the source and the detector being jointly moveable to different scan coordinates defined by at least one scan trajectory around an imaging region to acquire X-ray projection images at a plurality of the different scan coordinates in a dynamic mode while moving and also being jointly moveable to a predetermined reference coordinate to acquire an X-ray projection image at the predetermined reference coordinate in a static mode while resting, and
wherein:
each dynamic gain calibration parameter is obtained from an X-ray projection image acquired in the dynamic mode at one of the different scan coordinates of the at least one scan trajectory during a dynamic gain calibration period,
the static gain calibration parameter is obtained from the X-ray projection image acquired in the static mode at the predetermined reference coordinate during a static gain calibration period, and
a start time for the static gain calibration period occurs later than a start time for the dynamic gain calibration period such that the static gain calibration period and the dynamic gain calibration period are not overlapping in time.

12. The method according to claim 11, further comprising obtaining a further static gain calibration parameter, wherein:
the plurality of adjusted dynamic gain calibration parameters is determined based on the obtained plurality of dynamic gain calibration parameters, the obtained static gain calibration parameter, and the obtained further static gain calibration parameter,
the further static gain calibration parameter is obtained from an X-ray projection image acquired in the static mode at the predetermined reference coordinate during an initial static gain calibration period immediately following the dynamic gain calibration period, and
a start time for the initial static gain calibration period precedes the start time for the static gain calibration period such that the initial static gain calibration period and the subsequent static gain calibration period are not overlapping in time.

13. The method according to claim 11, further comprising:
performing a first X-ray calibration scan in the dynamic mode for the at least one scan trajectory during the dynamic gain calibration period to acquire first X-ray projection image data for each pixel element of the detector and for each scan coordinate of the at least one scan trajectory,
extracting a dynamic gain calibration parameter from the acquired first X-ray projection image data of each pixel element of the detector and for each scan coordinate of the at least one scan trajectory,
acquiring second X-ray projection image data for each pixel element of the detector in the static mode at the predetermined reference coordinate during the static gain calibration period, and
extracting the static gain calibration parameter from the acquired second X-ray projection image data of each pixel element of the detector for the predetermined reference coordinate.

14. The method according to claim 11, further comprising using the plurality of adjusted dynamic gain calibration parameters for at least one of image uniformity correction or image reconstruction of X-ray projection images acquired during a subject scan.

15. A non-transitory computer-readable storage medium having stored a computer program comprising instructions, which, when executed by a processor, cause the processor to:
obtain a plurality of dynamic gain calibration parameters as first inputs,
obtain a static gain calibration parameter as a second input, and
determine a plurality of adjusted dynamic gain calibration parameters corresponding to each of the plurality of dynamic gain calibration parameters based on at least the obtained plurality of dynamic gain calibration parameters and the obtained static gain calibration parameter,
wherein the X-ray system comprises a source and a detector including a plurality of pixel elements, the source and the detector being jointly moveable to different scan coordinates defined by at least one scan trajectory around an imaging region to acquire X-ray projection images at a plurality of the different scan coordinates in a dynamic mode while moving and also being jointly moveable to a predetermined reference coordinate to acquire an X-ray projection image at the predetermined reference coordinate in a static mode while resting, and
wherein:
each dynamic gain calibration parameter is obtained from an X-ray projection image acquired in the dynamic mode at one of the different scan coordinates of the at least one scan trajectory during a dynamic gain calibration period,
the static gain calibration parameter is obtained from the X-ray projection image acquired in the static mode at the predetermined reference coordinate during a static gain calibration period, and
a start time for the static gain calibration period occurs later than a start time for the dynamic gain calibration period such that the static gain calibration period and the dynamic gain calibration period are not overlapping in time.

16. The non-transitory computer-readable storage medium according to claim 15, wherein the instructions, when executed by the processor, further cause the processor to:
obtain a further static gain calibration parameter as a third input,
wherein:
the plurality of adjusted dynamic gain calibration parameters is determined based on the obtained plurality of dynamic gain calibration parameters, the obtained static gain calibration parameter, and the obtained further static gain calibration parameter,
the further static gain calibration parameter is obtained from an X-ray projection image acquired in the static mode at the predetermined reference coordinate during an initial static gain calibration period immediately following the dynamic gain calibration period, and
a start time for the initial static gain calibration period precedes the start time for the static gain calibration period such that the initial static gain calibration period and the subsequent static gain calibration period are not overlapping in time.

17. The non-transitory computer-readable storage medium according to claim 15, wherein the instructions, when executed by the processor, further cause the processor to:
perform a first X-ray calibration scan in the dynamic mode for the at least one scan trajectory during the dynamic gain calibration period to acquire first X-ray projection image data for each pixel element of the detector and for each scan coordinate of the at least one scan trajectory,
extract a dynamic gain calibration parameter from the acquired first X-ray projection image data of each pixel element of the detector and for each scan coordinate of the at least one scan trajectory,
acquire second X-ray projection image data for each pixel element of the detector in the static mode at the predetermined reference coordinate during the static gain calibration period, and
extract the static gain calibration parameter from the acquired second X-ray projection image data of each pixel element of the detector for the predetermined reference coordinate.

18. The non-transitory computer-readable storage medium according to claim 15, wherein the instructions, when executed by the processor, further cause the processor to use the plurality of adjusted dynamic gain calibration parameters for at least one of image uniformity correction or image reconstruction of X-ray projection images acquired during a subject scan.

19. The non-transitory computer-readable storage medium according to claim 15, wherein the instructions, when executed by the processor, further cause the processor to determine the plurality of adjusted dynamic gain calibration parameters at an end of the static gain calibration period or subsequently to the static gain calibration period.

20. The non-transitory computer-readable storage medium according to claim 16, wherein each of the plurality of adjusted dynamic gain calibration parameters and the corresponding dynamic gain calibration parameters is associated with a pixel element of the detector at one of the different scan coordinates and is determined according to a functional relationship: R=the first inputs * the second input/the third input, with the second input and the third input being associated with the pixel element of the detector at the predetermined reference coordinate.

\* \* \* \* \*